(12) United States Patent
Siskin et al.

(10) Patent No.: US 7,538,251 B2
(45) Date of Patent: May 26, 2009

(54) SYNTHESIS OF SEVERELY STERICALLY HINDERED SECONDARY AMINOETHER ALCOHOLS FROM A KETENE AND/OR CARBOXYLIC ACID HALIDE AND/OR CARBOXYLIC ACID ANHYDRIDE

(75) Inventors: Michael Siskin, Randolph, NJ (US); Alan Roy Katritzky, Gainesville, FL (US); Kostyantyn Mykolayevich Kirichenko, Gainesville, FL (US); Adeana Richelle Bishop, Baton Rouge, LA (US); Christine Nicole Elia, Bridgewater, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 222 days.

(21) Appl. No.: 10/587,204

(22) PCT Filed: Feb. 1, 2005

(86) PCT No.: PCT/US2005/003060

§ 371 (c)(1),
(2), (4) Date: Apr. 19, 2007

(87) PCT Pub. No.: WO2005/082836

PCT Pub. Date: Sep. 9, 2005

(65) Prior Publication Data

US 2007/0287866 A1    Dec. 13, 2007

Related U.S. Application Data

(60) Provisional application No. 60/545,195, filed on Feb. 17, 2004.

(51) Int. Cl.
*C07C 209/22*    (2006.01)
(52) U.S. Cl. ............... 564/393; 564/395; 564/396; 564/468; 564/469; 564/474
(58) Field of Classification Search .............. None
See application file for complete search history.

(56) References Cited

U.S. PATENT DOCUMENTS

| | | | |
|---|---|---|---|
| 4,112,051 A | 9/1978 | Sartori et al. | |
| 4,112,052 A | 9/1978 | Sartori et al. | |
| 4,405,585 A | 9/1983 | Sartori et al. | |
| 4,417,075 A | 11/1983 | Stogryn | |
| 4,471,138 A | 9/1984 | Stogryn | |
| 4,487,967 A | 12/1984 | Stogryn et al. | |
| 4,508,692 A | 4/1985 | Savage et al. | |
| 4,618,481 A | 10/1986 | Heinzelmann et al. | |
| 4,892,674 A | 1/1990 | Ho et al. | |
| 4,894,178 A | 1/1990 | Ho et al. | |
| 4,961,873 A | 10/1990 | Ho et al. | |
| 5,098,604 A | 3/1992 | Brouard et al. | |
| 5,874,623 A | 2/1999 | Adkins et al. | |
| 7,351,865 B2 * | 4/2008 | Siskin et al. ............... | 564/468 |
| 7,429,680 B2 * | 9/2008 | Siskin et al. ............... | 564/468 |
| 2007/0293705 A1 * | 12/2007 | Siskin et al. ............... | 564/508 |

FOREIGN PATENT DOCUMENTS

| | | |
|---|---|---|
| GB | 2 017 524 | 10/1979 |
| WO | WO 2005/081777 | 9/2005 |
| WO | WO 2005/082835 | 9/2005 |
| WO | WO 2005/082837 | 9/2005 |

OTHER PUBLICATIONS

Frazier and Kohl, "Selective Absorption of Hydrogen Sulfide from Gas Streams", Industrial and Engineering Chemistry, Nov. 1950, pp. 2288-2292, vol. 42, No. 11, The Fluor Corporation Ltd., Los Angeles, California.
Overberger and Sarlo, "Mixed Sulfonic-Carboxylic Anhydrides", J. Am. Chem. Soc., Mar. 4, 1963, pp. 2446-2448, vol. 85.
Karger and Mazur, "Cleavage of Ethers by Mixed Sulfonic-Carboxylic Anhydrides", J. Am. Chem. Soc., Jul. 3, 1968, pp. 3878-3879, 90:14.

* cited by examiner

*Primary Examiner*—Brian J Davis
(74) *Attorney, Agent, or Firm*—Joseph J. Allocca

(57) ABSTRACT

Severely sterically hindered secondary aminoether alcohols are prepared by a process comprising reacting a ketene with sulfuric acid to produce an anhydride which is then reacted with, to cleave the ring of, a dioxane to yield a cleavage product which is then aminated using an amine, followed by hydrolysis with a base to yield the desired severely sterically hindered secondary aminoether alcohol.

10 Claims, No Drawings

SYNTHESIS OF SEVERELY STERICALLY HINDERED SECONDARY AMINOETHER ALCOHOLS FROM A KETENE AND/OR CARBOXYLIC ACID HALIDE AND/OR CARBOXYLIC ACID ANHYDRIDE

This application is the U.S. National Phase filing of PCT Application No. PCT/US2005/003060 filed Feb. 1, 2005, which claims priority to U.S. Provisional Patent Application No. 60/545,195 filed Feb. 17, 2004.

FIELD OF THE INVENTION

The present invention relates to a process for the preparation of severely sterically hindered secondary aminoether alcohols.

DESCRIPTION OF RELATED ART

It is well-known in the art to treat gases and liquids, such as mixtures containing acidic gases including $CO_2$, $H_2S$, $CS_2$, HCN, COS and oxygen and sulfur derivatives of $C_1$ to $C_4$ hydrocarbons with amine solutions to remove these acidic gases. The amine usually contacts the acidic gases and the liquids as an aqueous solution containing the amine in an absorber tower with the aqueous amine solution contacting the acidic fluid countercurrently. Usually this contacting results in the simultaneous removal of substantial amounts of both the $CO_2$ and $H_2S$. U.S. Pat. No. 4,112,052, for example, utilizes a sterically hindered amine to obtain nearly complete removal of $CO_2$ and $H_2S$ acid gases. This process is particularly suitable for systems in which the partial pressures of the $CO_2$ and related gases are low. For systems where the partial pressure of $CO_2$ is high or where there are many acid gases present, e.g., $H_2S$, COS, $CH_3SH$, $CS_2$, etc., a process utilizing an amine in combination with a physical absorbent, referred to as a "non-aqueous solvent process" is practiced. Such a system is described in U.S. Pat. No. 4,112,051.

Selective removal of $H_2S$ from acid gas systems containing both $H_2S$ and $CO_2$, however, is very desirable. Such selective removal results in a relatively high $H_2S/CO_2$ ratio in the separated acid gas which facilitates the subsequent conversion of the $H_2S$ to elemental sulfur in the Claus process.

The typical reactions of aqueous secondary and tertiary amines with $CO_2$ and $H_2S$ can be represented as follows:

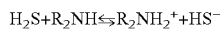

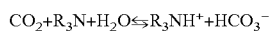

where R is the same or different organic radical and may be substituted with a hydroxyl group. Because the reactions are reversible they are sensitive to the $CO_2$ and $H_2S$ partial pressures which is determinative of the degree to which the reactions occur.

Selective $H_2S$ removal is particularly desirable in systems having low $H_2S/CO_2$ ratios and relatively low $H_2S$ partial pressures as compared to that of the $CO_2$. The ability of amine to selectivity remove $H_2S$ in such systems is very low.

Solutions of primary and secondary amines such as monoethanol-amine (MEA), diethanolamine (DEA), diisopropanolamine (DPA), and hydroxyethoxyethylamine (DEA) absorb both $H_2S$ and $CO_2$, and thus have proven unsatisfactory for the selective removal of $H_2S$ to the exclusion of $CO_2$. The $CO_2$ forms carbamates with such amines relatively easily.

$H_2S$ has been selectively removed from gases containing $H_2S$ and $CO_2$ by use of diisopropanolamine (DIPA) either alone or mixed with a non-aqueous physical solvent such as sulfolane. Contact times, however, must be kept short to take advantage of the faster reaction of $H_2S$ with the amine as compared to the rate of $CO_2$ reaction with the amine.

Frazier and Kohl, Ind. and Eng. Chem., 42, 2288 (1950) showed that the tertiary amine methydiethanolamine (MDEA) is more selective toward $H_2S$ absorption as compared to $CO_2$. $CO_2$ reacts relatively slowly with tertiary amines as compared to the rapid reaction of the tertiary amine with $H_2S$. However, it has the disadvantage of having a relatively low $H_2S$ loading capacity and limited ability to reduce the $H_2S$ content to the desired level at low $H_2S$ pressures encountered in certain gases.

UK Patent Publication No. 2,017,524 A discloses the use of aqueous solutions of dialkylmonoalkanolamines, e.g., diethylmonoethanol amine (DEAE), for the selective removal of $H_2S$, such material having higher selectivity and capacity for $H_2S$ removal at higher loading levels than MDEA. DEAE, however, has the disadvantage of a low boiling point of 161° C., making it relatively highly volatile resulting in large material loss.

U.S. Pat. No. 4,471,138 the entire teaching of which is incorporated herein by reference, teaches severely sterically hindered acyclic secondary aminoether alcohols having a high selectivity for $H_2S$ compared to $CO_2$. Selectivity is maintained at high $H_2S$ and $CO_2$ loadings.

The severely sterically hindered acyclic aminoether alcohols of U.S. Pat. No. 4,471,138 are represented by the general formula:

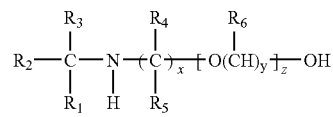

wherein $R_1$ and $R_2$ are each independently selected from the group consisting of alkyl and hydroxyalkyl radicals having 1-4 carbon atoms, $R_3$, $R_4$, $R_5$ and $R_6$ are each independently selected from the group consisting of hydrogen, alkyl, and hydroxyalkyl radicals having 1-4 carbon atoms, with the proviso that at least one of $R_4$ or $R_5$ bonded to the carbon atom which is directly bonded to the nitrogen atom is an alkyl or hydroxyalkyl radical when $R_3$ is hydrogen, x and y are each positive integers ranging from 2-4, and z is a positive integer ranging from 1-4. These materials are prepared by a high temperature reaction preferably in the presence of a solvent, of a secondary or tertiary alkyl primary amine with an ether alcohol containing a carbonyl functionality in the presence of a source of hydrogen or with a haloalkoxyalkanol. Preferably the composition is of the general formula:

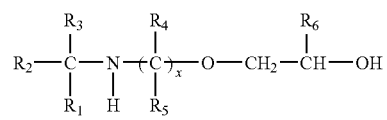

wherein:
$R_1=R_2=R_3=CH_3—$; $R_4=R_5=R_6=H$;
$R_1=R_2=R_3=CH_3—$; $R_4=H$ or $CH_3$; $R_5=R_6=H$;
$R_1=R_2=R_3=R_6=CH_3—$; $R_4=R_5=H$;
$R_1=R_2=R_3=CH_3CH_2—$; $R_4=R_5=R_6=H$; or
$R_1\neq R_2\neq R_3=H, CH_3—, CH_3CH_2—$; $R_4\neq R_5\neq R_6=H, CH_3—$;
and where x=2 or 3.

U.S. Pat. No. 4,487,967 is directed to a process for preparing severely sterically hindered secondary aminoether alcohols by reacting a primary amino compound with a polyalkenyl ether glycol in the presence of a hydrogenation catalyst at elevated temperatures and pressures. The primary amino compounds employed have a general formula:

where $R^1$ is selected from the group consisting of secondary or tertiary alkyl radicals having 3 to 8 carbon atoms or cycloalkyl radicals having 3 to 8 carbon atoms. The polyalkenyl ether glycols employed have the general formula:

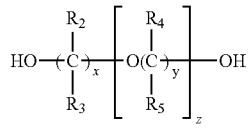

where $R_2$, $R_3$, $R_4$ and $R_5$ are each independently selected from the group consisting of hydrogen, $C_1$-$C_4$ alkyl radicals, and $C_3$-$C_8$ cycloalkyl radicals, with the proviso that if the carbon atom of $R_1$ directly attached to the nitrogen atom is secondary, at least one of $R_2$ and $R_3$ directly bonded to the carbon which is bonded to the hydroxyl group is as alkyl or cycloalkyl radical, x and y are each positive integers independently ranging from 2 to 4 and z is from 1 to 10, preferably 1 to 6, more preferably 1 to 4. The process is carried out in the presence of a catalytically effective amount of a supported Group VIII metal containing hydrogenation catalyst at elevated temperatures and pressure and the mole ratio of amino compound to polyalkenyl ether glycol is less than 2:1 when z is greater than 1.

SUMMARY OF THE INVENTION

Severely sterically hindered secondary aminoether alcohols of the general formula 1

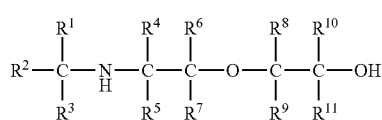

1 wherein $R^1$ and $R^2$ are each independently selected from the group consisting of alkyl and hydroxyalkyl radicals having 1 to 4 carbon atoms, preferably 1 to 2 carbon atoms, or $R^1$ and $R^2$ in combination with the carbon atom to which they are attached form a cycloalkyl group having 3 to 8 carbons; $R^3$ is selected from the group consisting of hydrogen, alkyl and hydroxyalkyl radicals having 1 to 4 carbon atoms, and mixtures thereof, preferably 1 to 2 carbon atoms, preferably alkyl or hydroxyalkyl radicals having 1 to 4 carbon atoms, more preferably 1 to 2 carbon atoms; $R^4$, $R^5$, $R^6$, $R^7$, $R^8$, $R^9$, $R^{10}$, and $R^{11}$ are the same or different and are selected from hydrogen, alkyl or hydroxyalkyl radicals having 1 to 4 carbon atoms, preferably 1 to 2 carbon atoms, or cycloalkyl radicals having 3 to 8 carbons; $R^4$, $R^5$, $R^6$, $R^7$, $R^8$, $R^9$, $R^{10}$, and $R^{11}$ are preferably hydrogen provided that when $R^3$ is hydrogen at least one of $R^4$ and $R^5$ bonded to the carbon which is directly bonded to the nitrogen atom is an alkyl or hydroxyalkyl radical, are prepared by a process involving reacting an organic carboxylic acid halide, an organic carboxylic acid anhydride or a ketene, or a mixture of any two or of all three thereof, of the formula 2:

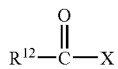
2a

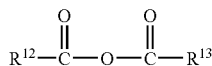
2b

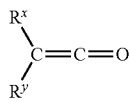
2c wherein $R^{12}$ and $R^{13}$ are the same or different and each is selected from the group consisting of alkyl radicals having 1 to 4 carbon atoms, preferably 1 to 2 carbon atoms, most preferably methyl, or aryl radicals, preferably phenyl substituted with hydrogen, one or more alkyl radicals having 1-10 carbon atoms, preferably 1-4 carbon atoms, most preferably methyl in the para position, and mixtures thereof, and x is a halogen selected from the group consisting of F, Cl, Br, I and mixtures thereof, preferably Cl, and wherein $R^x$ and $R^y$ are the same or different and are selected from the group consisting of hydrogen, alkyl radicals having 1-4 carbons, preferably 1 to 2 carbons, aryl radicals, preferably aryl radicals bearing substituents selected from the group consisting of hydrogen and one or more alkyl radicals having 1 to 10 carbons, preferably 1-4 carbons, and mixtures thereof, or $R^x$ and $R^y$ in combination with the carbon to which they are attached form a cycloalkyl radical having 3 to 8 carbons, preferably $R^x$ and $R^y$ are hydrogen or phenyl, with 50% sulfuric acid to fuming sulfuric acid, preferably 75% sulfuric acid to fuming sulfuric acid, more preferably 90% sulfuric acid to fuming sulfuric acid to produce monoacyl sulfate 3 and/or diacyl sulfate 4:

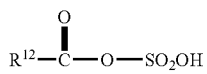
3a

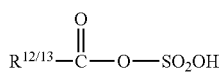
3b

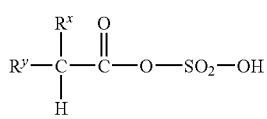
3c

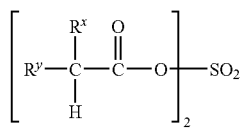
4a

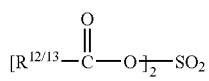
4b wherein $R^{12/13}$ means that in the product the R group can be $R^{12}$ or $R^{13}$, or mixtures thereof, which are then reacted with a 1,4-dioxane of the formula 5:

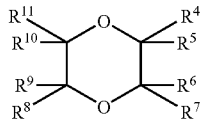

5 wherein $R^4$, $R^5$, $R^6$, $R^7$, $R^8$, $R^9$, $R^{10}$, and $R^{11}$ are the same or different and are selected from hydrogen, alkyl and hydroxyalkyl radicals having 1 to 4 carbons, and mixtures thereof, preferably 1-2 carbons, and mixtures thereof, more preferably $R^4$, $R^5$, $R^6$, $R^7$, $R^8$, $R^9$, $R^{10}$, and $R^{11}$ are hydrogen, to yield material of the general formula 6 and/or 7:

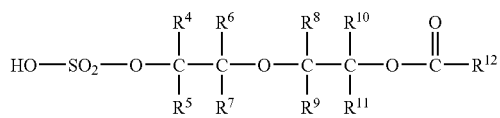

6a

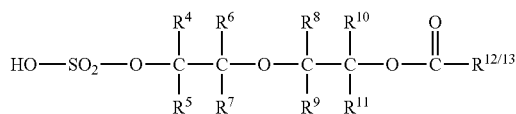

6b

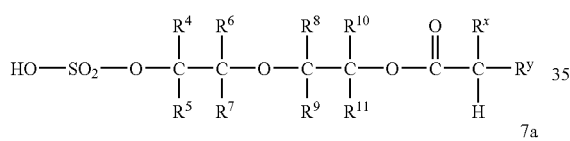

6c

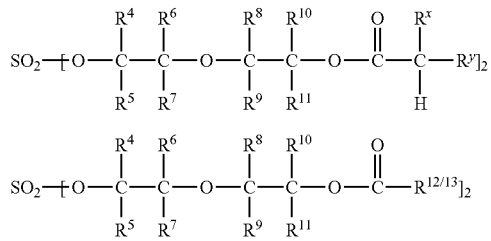

7a

7b or mixtures thereof. It is not necessary that the product from each reaction step be isolated before being reacted with the reactant of a subsequent reaction step up to this point. A cleavage product is produced. The mixing of the organic carboxylic acid halide, organic carboxylic acid anhydride, ketene or mixture thereof, with the sulfuric acid and the dioxane can be in any order or sequence. Thus, the anhydride, and halide, ketene or mixture thereof, can be mixed with the sulfuric acid and then mixed with the dioxane, or the dioxane can be first mixed with the sulfuric acid and then the anhydride, acid halide, ketene, or mixture thereof, can be added, or the anhydride, acid halide, ketene or mixture thereof can be mixed with the dioxane followed by the addition of the sulfuric acid. Thus, the combination of the anhydride, acid halide, ketene or mixture thereof with the dioxane and the sulfuric acid can be combined into a single reaction mixture and reacted as a mixture resulting in the one step production of the desired cleavage product. This cleavage product is then aminated using an alkyl amine of the formula 8

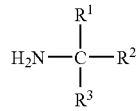

8 wherein $R^1$ and $R^2$ are the same of different and selected from the group consisting of alkyl and hydroxyalkyl radicals having 1 to 4 carbon atoms, and mixtures thereof, preferably 1 to 2 carbon atoms, more preferably methyl, or $R^1$ and $R^2$ in combination with the carbon atom to which they are attached form a cycloalkyl group having 3 to 8 carbons, and mixtures thereof; $R^3$ is selected from the group consisting of hydrogen, alkyl and hydroxyalkyl radicals having 1 to 4 carbon atoms, and mixtures thereof, preferably 1 to 2 carbon atoms, preferably alkyl or hydroxyalkyl radicals having 1 to 4 carbon atoms, more preferably 1 to 2 carbon atoms, most preferably methyl, provided that when $R^3$ is hydrogen then at least one of $R^4$ and $R^5$ is an alkyl or hydroxyalkyl radical, to yield material of the general formula 9:

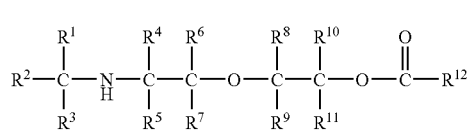

9a

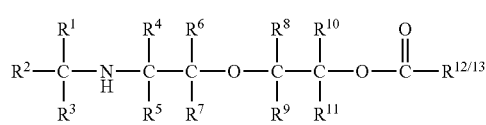

9b

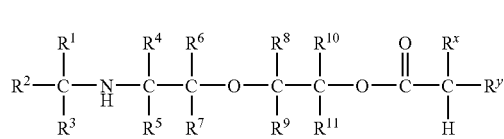

9c or mixtures thereof, which is then hydrolyzed with base to yield 1:

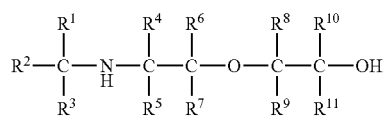

1

The preferred compounds defined by the general formula 1 include:

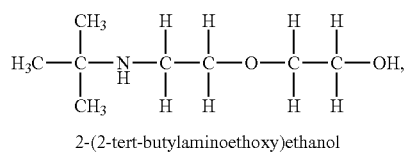

2-(2-tert-butylaminoethoxy)ethanol

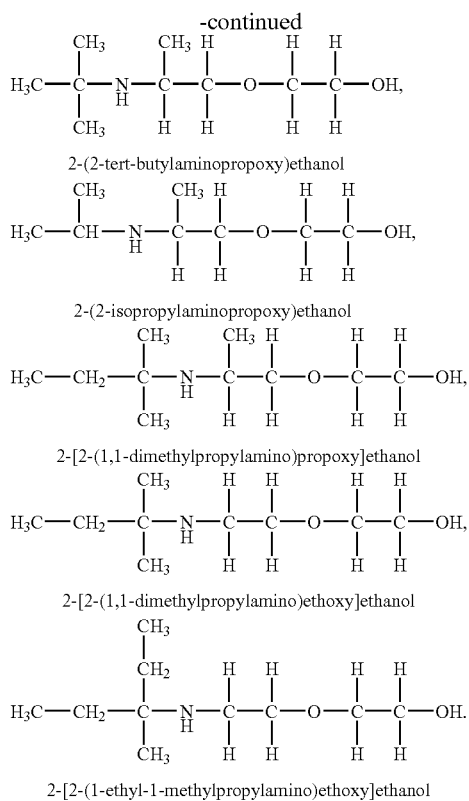

2-(2-tert-butylaminopropoxy)ethanol 2-(2-isopropylaminopropoxy)ethanol

2-[2-(1,1-dimethylpropylamino)propoxy]ethanol

2-[2-(1,1-dimethylpropylamino)ethoxy]ethanol

2-[2-(1-ethyl-1-methylpropylamino)ethoxy]ethanol

Typical starting materials are ketenes represented by the formula 2:

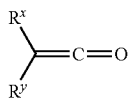

2 wherein $R^x$ and $R^y$ are the same or different and are selected from the group consisting of hydrogen, alkyl radicals having from 1 to 4 carbons, preferably 1 to 2 carbons, most preferably hydrogen, aryl radicals, preferably aryl radicals bearing substituents selected from the group consisting of hydrogen, one or more alkyl radicals having 1 to 10 carbons, preferably 1 to 4 carbons, and mixtures thereof, or $R^x$ and $R^y$ in combination with the carbon to which they are attached form a cycloalkyl radical having 3 to 8 carbons, and mixtures thereof, preferably $R^x$ and $R^y$ are hydrogen or phenyl.

The ketenes useful in the present invention can be prepared employing any of the processes typical in the art. Thus, for example, acetic acid can be subjected to high temperature dehydration in the presence of $AlPO_4$, or acetone can be subjected to pyrolysis at from 500-750° C. to yield ketene and methane.

The ketene, organic carboxylic acid halide, organic carboxylic acid anhydride, or mixtures of any two or all three thereof, is reacted with 50% to fuming, preferably 75% to fuming, most preferably 90% to fuming sulfuric acid, $H_2SO_4$, at preferably a 1:1 molar ratio to form the monoacyl sulfate 3 or in about a 2:1 molar ratio to form the diacyl sulfate 4. Excess sulfuric acid can be used at the practitioners discretion, but the use of excess acid would necessitate the practice of an additional separation step. The use of about a stoichiometric ratio, therefore, is preferred. The use of concentrated sulfuric acid (90% to fuming) is preferred. Fuming sulfuric acid I also known as oleum. It is a solution of sulfur trioxide in 100% sulfuric acid. 100% sulfuric acid is also referred to as monohydrate because it constitutes one molecule of $SO_3$ combined with one molecule of $H_2O$. The percent of free $SO_3$ is used as a measure of oleum or fuming sulfuric acid strength. Thus, 20% fuming sulfuric acid constitutes 20% free $SO_3$ over and above the 100% sulfuric acid carrier solvent. Twenty (20)% fuming sulfuric acid contains 20% $SO_3$ and 80% $H_2SO_4$ (of 100% concentrated $H_2SO_4$) by weight. Oleum or fuming sulfuric acid can contain as high as 80%+free $SO_3$. Reaction can be conducted at about –80° C. to about 150° C., preferably about –20° C. to about 125° C. at a pressure between about 1 bar to 100 bars, preferably about 1 bar to 50 bars, more preferably about 1 bar to 10 bars. The reaction can be carried out in an inert solvent such as sulfolane, hexanes, acetonitrile. Preferably the dioxane for the subsequent cleavage reaction is used as the solvent resulting in a unified first step wherein the reaction mixture contains the carboxylic acid halide, the organic carboxylic acid anhydride, the ketene or mixture thereof, the sulfuric acid and the dioxane. This reaction mixture is then reacted under the condition subsequently described for the dioxane cleavage reaction.

Acyl sulfate 3 or 4 is then reacted with a dioxane 5 which is typically of the formula:

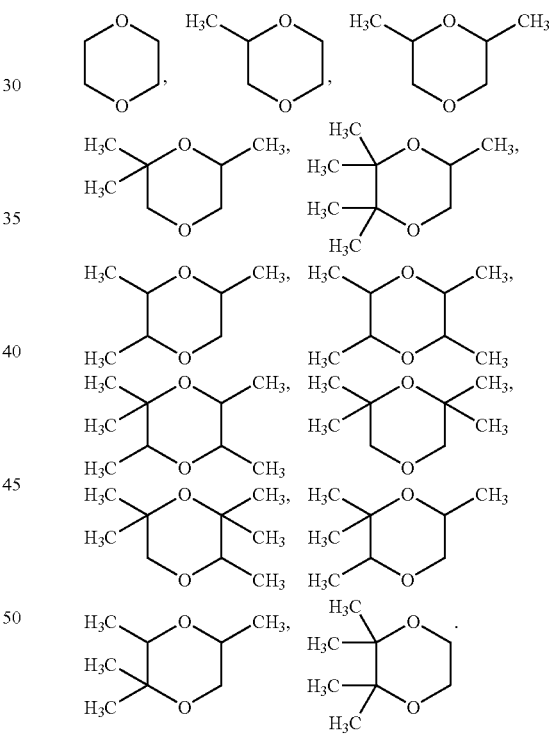

Other substituted isomers can be readily envisioned. Preferably, the dioxane is

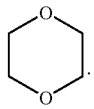

Cleavage of the dioxane ring and reaction is for a time sufficient to achieve about 60-90% conversion to product.

The reaction can be carried out either in the absence of solvent, in which case the dioxane serves as the solvent for the reaction, or in a solution containing an additional inert solvent such as acetonitrite or toluene, the reaction being conducted at temperatures of from about −80° C. to about 200° C.

Preferably, the dioxane serves as the solvent for the reaction. The molar ratio of dioxane to acyl sulfate, for the reaction of dioxane with acyl sulfate 3 is about 1:1 to about 10:1, preferably about 1:1 to about 8:1, most preferably about 1:1 to about 5:1, while the molar ratio of dioxane to acyl sulfate of formula 4 is about 2:1 to about 10:1, preferably about 2:1 to about 8:1, more preferably about 2:1 to about 5:1. Expressed differently, the dioxane to acyl sulfate ratio is about stoichiometric to about 10:1, preferably about stoichiometric to about 8:1, more preferably about stoichiometric to about 5:1. The temperature for the reaction of dioxane with acyl sulfate of general formula 3 is in the range of between about −80° C. to about 200° C., preferably about −20° C. to about 160° C., most preferably about −20° C. to about 50° C., and the temperature for the reaction of dioxane with the acyl sulfate of general formula 4 is in the range of between about 50° C. to about 200° C., preferably about 70° C. to about 160° C., more preferably about 80° C. to about 140° C.

The ether cleavage process is described in greater detail by Karger and Mazur in "The Cleavage of Ethers by Mixed Sulfonic-Carboxylic Anhydrides", Journal of the American Chemical Society, 1968, 90, 3878-3879. See also, "Mixed sulfonic-carboxylic anhydrides. I. Synthesis and thermal stability. New syntheses of sulfonic anhydrides" Journal of Organic Chemistry, 1971, 36, 528; and "Mixed sulfonic-carboxylic anhydrides. II. Reactions with aliphatic ethers and amines" Journal of Organic Chemistry, 1971, 36, 532.

The reaction of a dioxane 5 with acyl sulfate 3 yields cleavage product of general formula 6, while the reaction of a dioxane 5 with diacyl sulfate 4 yields a cleavage product of the formula 7.

The cleavage products 6 and 7 are then aminated using an amine 8, typically of the formulae:

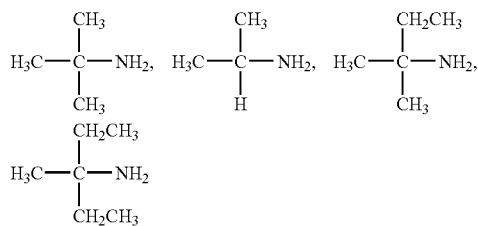

preferably:

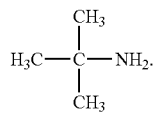

for a time sufficient to replace the sulfate group in cleavage products 6 and 7 with an amine 8. In the case of the amination of cleavage product 7, at least two moles of the amine 8 are required for each mole of 7. In general, the amine to cleavage product sulfonate group mole ratio is in the range of about stoichiometric to about 10:1, preferably about stoichiometric to about 8:1, more preferably about stoichiometric to about 4:1. In the case of the amination of either product 6 or product 7, the same aminated product 9 is produced:

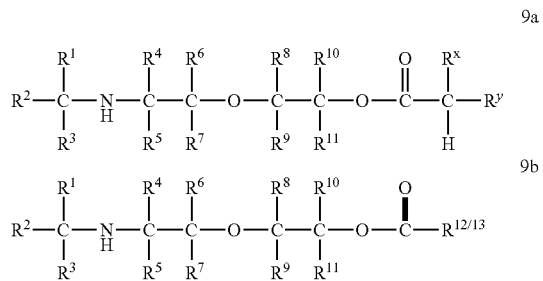

This amination step can be carried out under any conditions typical in the art. Amination can be conducted at atmosphere or at elevated pressure, elevated pressure being especially suitable when amination is to be performed using relatively low boiling amines such at t-butylamine.

Thus, amination can be conducted at pressures of from about atmospheric (1 bar) to about 100 bars, preferably about 1 to about 50 bars and at temperatures of from about 40° C. to about 200° C., preferably about 40° C. to about 125° C. The process can be performed under reflux but this is not absolutely necessary. An inert solvent optionally can be used such as benzene, toluene, diethyl ether, hexanes, and the like.

This aminated product 9 is hydrolyzed to product 1 using a base, which is typically an alkali metal hydroxide, alkali metal carbonate, alkali metal alkoxide, such as sodium hydroxide, sodium carbonate, sodium methoxide, sodium tert-butoxide, etc. Reaction is conducted at about 20° C. to about 110° C., preferably about 20° C. to about 50° C. The process can be conducted under reflux. Solvents which can be used if either necessary or simply desirable include water and alcohols and mixtures thereof. The alcohol can be the same as that from which the alkoxide base is derived, i.e., methanol in the solvent for alkali metal methoxide.

EXAMPLES

The preparation of 2-(2-tert-butylaminoethoxy)ethanol (EETB). A 100 mL one-necked flask was charged with 1,4-dioxane (20 g, 0.23 mol, 20 mL) under a nitrogen atmosphere; acetic anhydride (4 mL, 4.28 g, 42 mmol) was added followed by the addition of 20% fuming sulfuric acid (1.04 mL, 2.0 g; contains 16.4 mmol of $H_2SO_4$) at room temperature. The reaction mixture was refluxed at 101° C. and checked by NMR. The $^1$H NMR spectrum showed that products of cleavage reached a maximum after 18 h. The reaction mixture was evaporated under vacuum to dryness (bath 50° C., 15 mm of Hg). Toluene (50 mL) was added to the residue followed by the addition of tert-butylamine (30 mL, 21 g, 0.29 mol) at room temperature. The reaction mixture was gently (tert-butylamine BP=44-46° C.) refluxed for 30 h. Then, the reaction mixture was cooled to room temperature and filtered; the precipitate was washed with toluene. The filtrate was partially evaporated under vacuum to remove tert-butylamine. The residue was filtered and the precipitate was washed with toluene. The filtrate was evaporated under vacuum to give a yellow residual oil (4.5 g). The NMR spectra showed 2-(2-t-butylaminoethoxy)ethyl acetate of 60-70% purity. The character of signals in $^1$H NMR spectrum suggests 2-(2-hydroxyethoxy)ethyl acetate as major impurity (signal of acetoxy group: singlet at 2.09 ppm, of etheral signals: m, 3.65-3.72 ppm, and ester signal: m, 4.21-4.27 ppm), as result of incomplete amination or hydrolysis during work up.

The reflux of 2-(2-t-butylaminoethoxy)ethyl acetate (2 g, 10 mmol) with 15 mmol of NaOH in methanol (10 mL) for 6 h followed by evaporation under vacuum, extraction with diethyl ether and removing of solvent under vacuum gave 1.6 g of yellow oil, the NMR of which confirmed 2-(2-tert-butylaminoethoxy)ethanol (EETB) of 70-75% purity. The EETB is probably contaminated with diethylene glycol (extra protons in the range 3.59-3.73 ppm; by comparison with NMR data for diethylene glycol: 3.60 ppm, m, 4H; 3.74 ppm, m, 4H).

The cleavage of 1,4-dioxane with diaetyl sulfate generated from fuming sulfuric acid and a twofold excess of acetic anhydride. The same reaction conditions were used as for the cleavage above using 20% fuming sulfuric acid and acetic anhydride (twofold excess: 1 equivalent for $SO_3$, plus 2 equivalent for $H_2SO_4$, and plus 100% excess). Also, the amination with t-$BuNH_2$ was carried out in an autoclave (bomb) to provide maximum completeness.

A 100 mL one-necked flask was charged with 1,4-dioxane (30 g, 0.35 mol, 30 mL) under a nitrogen atmosphere; acetic anhydride (7.1 mL, 7.66 g, 75 mmol was added followed by the addition of 20% fuming sulfuric acid (1.04 mL, 2.0 g; contains 0.4 g, 5.0 mmol of $SO_3$ and 1.6 g, 16.4 mmol of $H_2SO_4$) at room temperature. The reaction mixture was refluxed for 40 h and checked by NMR. The $^1$H NMR spectrum showed the presence of products of cleavage. Reflux was continued for an additional 8 h. The NMR showed the same set of signals as after 40 h. The reaction mixture was evaporated under vacuum to dryness (the reaction mixture was protected from contact with moisture; the solvent was directly evaporated into a dry-ice trap using a dry membrane-type vacuum pump; bath 50° C., 5 mm of Hg). Toluene (50 mL) was added to the residue followed by the addition of tert-butylamine (30 mL, 21 g, 0.29 mol) at room temperature. The reaction mixture was stirred for 5 min and the reaction mixture was transferred into an autoclave (bomb) and stirred at approximately 170° C. (175-180° C. in the oil bath) for 13 h. The reaction mixture was cooled to room temperature and filtered from the precipitate. The precipitate was washed with toluene and the combined filtrate was evaporated in vacuum. Toluene was added to the residue and the mixture was washed with an aqueous solution of sodium carbonate. The organic layer was dried over magnesium sulfate and the solvent was evaporated in vacuum to give 3.4 g of yellow oil. The $^1$H NMR analysis showed the desired 2-(2-t-butylaminoethoxy) ethylacetate product in 70-75% purity. As in the previous reaction, the major byproduct is 2-(2-hydroxyethoxy)ethyl acetate; extra protons at 2.09 ppm (0.7 H, Ac), 3.58-3.72 (3H) and 4.20-4.24 (0.45 H, $CH_2OAc$). Part of this product crystallized as colorless needles).

Cleavage of 1,4-dioxane with diacetyl sulfate generated from fuming sulfuric acid and acetic anhydride (1 equivalent of acetic anhydride for $SO_3$, plus 2 equivalent for $H_2SO_4$) at 120° C. A 15 mL sealed tube was charged with 1,4-dioxane (10 g, 0.11 mol, 10 mL) and acetic anhydride (2.67 mL, 2.88 g, 28.2 mmol) was added followed by the addition of 20% fuming sulfuric acid (0.78 mL, 1.5 g; contains 0.3 g, 3.75 mmol of $SO_3$ and 1.2 g, 12.23 mmol of $H_2SO_4$) at room temperature under a nitrogen atmosphere. The reaction mixture was stirred at 120-122° C. for 24 hours and checked by NMR. The $^1$H NMR spectrum showed presence of products of cleavage. The reaction mixture was evaporated under vacuum to dryness. Toluene (50 mL) was added to the residue followed by the addition of tert-butylamine (17 mL, 11.8 g, 0.16 mol) at room temperature. The reaction mixture was gently refluxed for 24 h, cooled to room temperature and filtered from the precipitate. The precipitate was washed with toluene and the combined filtrates were evaporated under vacuum. Toluene was added to the residue and the mixture was washed with an aqueous solution of sodium carbonate. The organic layer was dried over magnesium sulfate and the solvent was evaporated under vacuum to give 3.5 g of brown oil. The $^1$H NMR analysis showed the desired product 2-(2-tert-butylaminoethoxy)ethyl acetate of approximately 70% purity. The major by-products are 2-(2-hydroxyethoxy)ethyl acetate or 2-(2-acetoxyethoxy)ethyl acetate.

Cleavage of 1,4-dioxane with diacetyl sulfate generated from sulfur trioxide and acetic anhydride. A 15 mL sealed tube was charged with dioxane (10 g, 0.115 mol), acetic anhydride (1.81 mL, 1.96 g, 19 mmol), and sulfur trioxide (1.54 g, 19 mmol) under a nitrogen atmosphere. The mixture was stirred at 119-123° C. for 5 h (brown clear solution). The $^1$H NMR analysis showed characteristic signals of cleavage products. The reaction mixture was concentrated under vacuum. The residue was stirred with tert-butyl amine (20 mL, 13.92 g, 0.19 mol) in toluene (30 mL) under gentle reflux for 24 h. The reaction mixture was cooled to room temperature, filtered, and the precipitate was washed with toluene. The filtrate was evaporated and the product was extracted with toluene. The extract was evaporated under vacuum to give 2 g of yellow-brown oil. The NMR test showed desired product 2-(2-tert-butylaminoethoxy)ethyl acetate of approximately 65% purity.

The invention claimed is:

1. A method for the synthesis of severely sterically hindered secondary aminoether alcohols of the formula

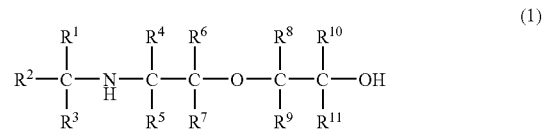

wherein $R^1$ and $R^2$ are each selected from the group consisting of alkyl, hydroxylalkyl radicals having 1 to 4 carbon atoms or in combination with the carbon atom to which they are attached they form a cycloalkyl group having 3 to 8 carbon atoms, and $R^3$ is selected from the group consisting of hydrogen, alkyl and hydroxyalkyl radicals having 1 to 4 carbon atoms, and mixtures thereof, and $R^4$, $R^5$, $R^6$, $R^7$, $R^8$, $R^9$, $R^{10}$ and $R^{11}$ are the same or different and are selected from the group consisting of hydrogen, alkyl and hydroxyalkyl radicals having 1 to 4 carbons provided that at least one of $R^4$ or $R^5$ bonded to the carbon atom directly bonded to the nitrogen atom is an alkyl or hydroxyalkyl radical when $R^3$ is hydrogen, the process involving reacting an organic carboxylic acid halide, an organic carboxylic acid anhydride, a ketene, or a mixture of any two or of all three thereof, of the formula

wherein $R^{12}$ and $R^{13}$ are the same or different and are selected from the group consisting of alkyl radicals having 1 to 4 carbon atoms, aryl radicals bearing hydrogen or $C_1$ to $C_{10}$ alkyl radicals substituted thereon, and mixtures thereof, X is a halogen selected from the group consisting of F, Cl, Br, I, and mixtures thereof, and $R^x$ and $R^y$ are the same or different and are selected from the group consisting of hydrogen, alkyl radicals having 1-4 carbons, aryl radicals, aryl radicals bearing substituents selected from the group consisting of hydrogen and one or more alkyl radicals having 1 to 10 carbons, and mixtures thereof, or $R^x$ and $R^y$ in combination with the carbon to which they are attached form a cycloalkyl radical having 3 to 8 carbons, with 50% sulfuric acid to fuming sulfuric acid to yield monoacylsulfate (3) and/or diacylsulfate (4) of the formula

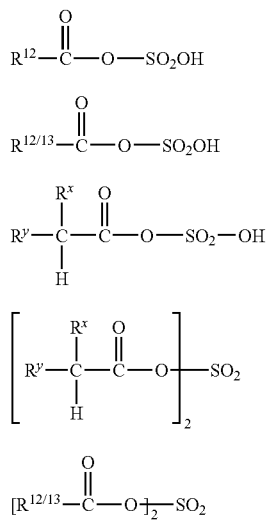

3a
3b
3c
4a
4b which is then reacted with a dioxane of the formula

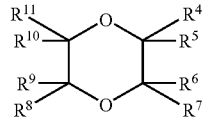

5 wherein $R^4$, $R^5$, $R^6$, $R^7$, $R^8$, $R^9$, $R^{10}$, and $R^{11}$ are the same or different and are selected from hydrogen, alkyl and hydroxyalkyl radicals having 1 to 4 carbons to yield products of the structure 6 and/or 7:

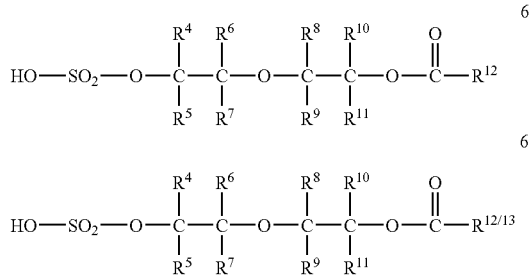

6a
6b

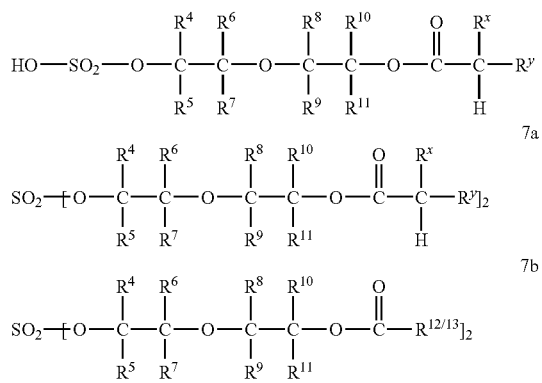

6c
7a
7b and mixtures thereof, which are then aminated with an alkyl amine of the formula

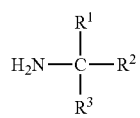

8 wherein $R^1$, $R^2$ and $R^3$ are as previously defined to yield material of the general formula 9

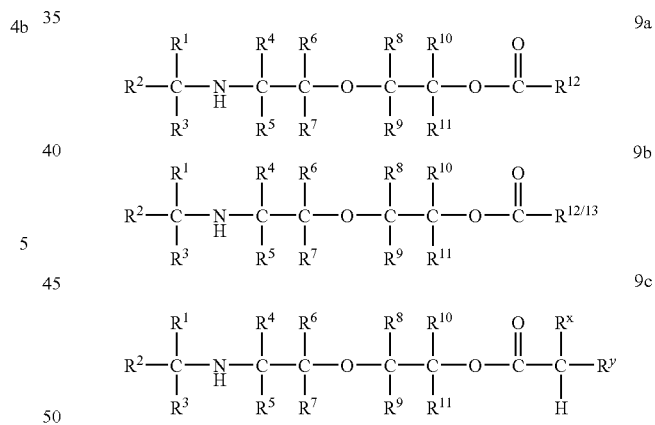

9a
9b
9c or mixtures thereof, which is then hydrolyzed with base to yield product (1).

2. The method of claim 1 for the synthesis of severely sterically hindered secondary aminoether alcohols using the organic carboxylic acid halide of the formula

2a

3. The method of claim 1 for the synthesis of severely sterically hindered secondary aminoether alcohols using the organic caraboxylic acid anhydride of the formula

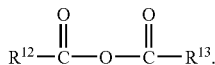

4. The method of claim 1 for the synthesis of severely sterically hindered secondary aminoether alcohols using a ketene of the formula

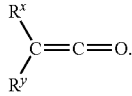

5. The method according to claim 1, 2, 3 or 4 wherein $R^1$, $R^2$, and $R^3$ are methyl radicals.

6. The method according to claim 1, 2, 3 or 4 wherein $R^4$, $R^5$, $R^6$, $R^7$, $R^8$, $R^9$, $R^{10}$ and $R^{11}$ are hydrogen, and $R^x$ and $R^y$ are hydrogen or phenyl.

7. The method according to claim 1, 2, 3 or 4 wherein the base is selected from alkali metal hydroxide, alkali metal alkoxide, or alkali metal carbonate.

8. The method according to claim 1, 2, 3 or 4 wherein $R^1$, $R^2$, and $R^3$ are methyl, $R^4$, $R^5$, $R^6$, $R^7$, $R^8$, $R^9$, $R^{10}$ and $R^{11}$ are hydrogen and $R^x$ and $R^y$ are hydrogen or phenyl.

9. The method according to claim 1, 2, 3 or 4 wherein the ketene, organic carboxylic acid halide, organic carboxylic acid anhydride, mixture of any two or of all three thereof, and the $H_2SO_4$ are reacted in about a stoichiometric ratio at a temperature between about −80° C. to about 150° C., the resulting sulfate is reacted with the dioxane at a dioxane to sulfate ratio of about stoichiometric to about 10:1 to cleave the dioxane at a temperature between about −80° C. to about 200° C., the resulting cleavage product is reacted with the alkyl amine in an amine to cleavage product mole ratio of about stoichiometric to about 10:1 at a pressure of from about atmospheric (1 bar) to about 100 bars, at a temperature of between about 40° C. to about 200° C., and the aminated product is hydrolyzed with base at between about 20° C. to about 110° C.

10. The method according to claim 1, 2, 3 or 4 wherein the mixing of the ketene, organic carboxylic acid halide, organic carboxylic acid anhydride, mixture of any two or of all three, the sulfuric acid and the dioxane are combined in a single step, the reaction mixture being heated at a temperature of between about −80° C. to about 200° C. to produce a cleavage product, the cleavage product and the alkylamine are reacted at an amine to cleavage product ratio ranging from about stoichiometric to about 10:1 at a pressure from about atmospheric (1 bar) to about 100 bars at a temperature of between about 40° C. to about 200° C., and the aminated product is hydrolyzed with base at between about 20° C. to about 110° C.

* * * * *